US007658915B2

(12) United States Patent
Freyman

(10) Patent No.: US 7,658,915 B2
(45) Date of Patent: Feb. 9, 2010

(54) SELECTED CELL DELIVERY FOR HEART FAILURE

(75) Inventor: Toby Freyman, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 579 days.

(21) Appl. No.: 11/493,711

(22) Filed: Jul. 24, 2006

(65) Prior Publication Data

US 2006/0263341 A1 Nov. 23, 2006

Related U.S. Application Data

(63) Continuation of application No. 10/198,101, filed on Jul. 19, 2002, now Pat. No. 7,097,833.

(51) Int. Cl.
*C12N 5/00* (2006.01)
*A01N 65/00* (2006.01)
*A61K 9/00* (2006.01)

(52) U.S. Cl. ............ 424/93.7; 424/93.1; 424/400; 435/325

(58) Field of Classification Search .................. None
See application file for complete search history.

(56) References Cited

U.S. PATENT DOCUMENTS

| 2002/0061587 A1 | 5/2002 | Anversa |
| 2002/0098167 A1 | 7/2002 | Anversa et al. |
| 2003/0003085 A1 | 1/2003 | Kunkel et al. |
| 2003/0054973 A1 | 3/2003 | Anversa |

FOREIGN PATENT DOCUMENTS

| WO | WO 00/17657 | 3/2000 |
| WO | WO 01/19379 | 3/2001 |
| WO | WO 01/27245 | 4/2001 |

OTHER PUBLICATIONS

Anversa et al., "Myocyte Growth and Cardiac Repair", J. Mol. Cell Cardiol., vol. 34, 2002, pp. 91-105.
Arbatli et al., "Cardioscopy and Robotic Assistance for the Diagnosis of Intraventricular Endocarditis", J. Heart Valve Dis., vol. 10, No. 5, Sep. 2001, pp. 686-688.
Bao et al., "Intramyocardial Delivery of FGF2 in Combination With Frequency Transmyocardial Revascularization", Catheterization and Cardiovascular Interventions, vol. 53, 2001, pp. 429-434.
Grossman et al., "Incomplete Retention After Direct Myocardial Injection," Catheterization and Cardiovascular Interventions, vol. 55, 2002, pp. 392-397.
Hierlihy et al., "The post-natal heart contains a myocardial stem cell population," FEBS Letters, vol. 530, 2002, pp. 239-243.
Koke et al. "Release of lactate dehydrogenase during isolation of adult rat heart cells," Cytobios, vol. 29, 1980, pp. 183-189.
Urbanek et al., "Intense myocyte formation from cardiac stem cells in human cardiac hypertrophy," PNAS, vol. 100, No. 18, Sep. 2, 2003, pp. 10440-10445.
Urbanek et al., "Myocardial regeneration by activation of multipotent cardiac stem cells in ischemic heart failure," PNAS, vol. 102, No. 24, Jun. 14, 2005, pp. 8692-8697.
Young, "Preparation of Isolated Cells from Rat Heart," Experientia, vol. 32, 1976, pp. 1389-1390.
Goodell M., "Blood," The Journal of the American Society of Hematology, vol. 94, No. 8, (Oct. 15, 1999), 2545-2547.
Goodell M. et al., "Isolation and Functional Properties of Murine Hematopoietic Stem Cells that are Replicating In Vivo," The Journal of Experimental Medicine, The Rockefeller University Press, vol. 183, (Apr. 1996), pp. 1797-1806.
Gussoni E. et al., "Dystrophin expression in the mdx mouse restored by stem cell transplantation," Nature, vol. 401, (Sep. 23, 1999), pp. 390-394.
Huss R., "CD34 stem cells as the earliest precursors of hematopoietic progeny," Experimental Hematology, vol. 26, (1998) pp. 1022-1023.
Jackson K. et al., "Regeneration of ischemic cardiac muscle and vascular endothelium by adult stem cells," The Journal of Clinical Investigation, vol. 107, No. 11, (Jun. 2001), pp. 1395-1402.
Kamihata H. et al., "Implantation of Bone Marrow Mononuclear Cells Into Ischemic Myocardium Enhances Collateral Perfusion and Regional Function via Side Supply of Angioblasts, Angiogenic Ligands, and Cytokines," Circulation (2001) pp. 1046-1052, vol. 104.
Kocher A.A. et al., "Neovascularization of ischemic myocardium by human bone marrow-derived angioblasts prevents cardiomyocyte apoptosis, reduces remodeling and improves cardiac function," Nature Medicine, vol. 7, No. 4 (Apr. 2001), pp. 430-436.

(Continued)

*Primary Examiner*—Christopher R Tate
*Assistant Examiner*—Aaron J Kosar
(74) *Attorney, Agent, or Firm*—Kenyon & Kenyon LLP

(57) ABSTRACT

This invention provides methods of increasing blood flow to tissue in a subject in need thereof, methods of regenerating tissue in a subject, methods of treating diseased tissue in a subject, methods of forming new blood vessels in tissue and new tissue, such as myocardial tissue, in a subject in need thereof, methods of increasing angiogenesis in diseased tissue in a subject, and methods of preventing heart failure in a subject, which methods comprise: a) isolating autologous mononuclear cells from the subject; b) selecting from the isolated autologous mononuclear cells of step (a) lineage negative (Lin⁻) mononuclear cells; and c) transplanting locally into or adjacent to the tissue an effective amount of the Lin⁻ autologous mononuclear cells, resulting in formation of new blood vessels in the tissue and formation of new tissue. Additional methods provided for such uses further select from the isolated autologous mononuclear cells of step (a) lineage negative (Lin⁻) mononuclear cells a subset of Lin⁻ mononuclear side population (SP) cells and transplant locally into or adjacent to the tissue an effective amount of the Lin⁻ SP cells. In other aspects, methods using tissue other than mononuclear cells for these uses are provided, which comprise (a) obtaining a cell suspension from the tissue or a second tissue of the subject; (b) selecting from the cell suspension step (a) side population (SP) cells; and (c) transplanting locally into or adjacent to the tissue an effective amount of the SP cells, resulting in formation of new blood vessels in the tissue and formation of new tissue.

24 Claims, No Drawings

OTHER PUBLICATIONS

Orlic D. et al., "Bone marrow cells regenerate infarcted myocardium", Nature, vol. 410, (Apr. 5, 2001), pp. 701-705.

Orlic D. et al., "PNAS USA 98", (2001), pp. 10344-10349.

Otani A. et al., "Bone Marrow-derived stem cells target retinal astrocytes and can promote or inhibit retinal angiogenesis", Nature Medicine, vol. 8, No. 9, (Sep. 2002), pp. 1004-1010.

Sato T. et al., "Reversible Expression of CD34 by Murine Hematopoietic Stem Cells", Blood, vol. 94, No. 8 (Oct. 15, 1999, pp. 2548-2554.

Steinberg D., "Precursor Cells to the Rescue", The Scientist (Nov. 27, 2000), p. 24.

Steinberg D., "Stem Cells Tapped to Replenish Organs", The Scientist (Nov. 27, 2000), pp. 20-21, 24.

Zanjani E. D., "Human bone marrow CD34$^-$ cells engraft in vivo and undergo multilineage expression that includes giving rise to CD34$^+$ cell", Experimental Hematology, vol. 26, (1998), pp. 353-360.

Liu, et al., "Phenotypic and in vitro characterization of Hoechst 33342 side population in umbilical cord blood", Blood, vol. 96, No. 11, part 1, Nov. 16, 2000, Abstract.

Mahmud Nadim et al., "The hematopoietic cellular potential of primate skeletal muscle cells", Blood, vol. 96, No. 11, part 1, Nov. 16, 2000, Abstract.

Josefsen et al., "Hematopoietic side population (SP) cells are present in highly purified human CD34+ cells from peripheral blood progenitor cells (PBPC)," Blood, vol. 98, No. 11, part 2, Nov. 16, 2001, Abstract.

Jackson et al., PNAS 96(25): 14482-14486 (Dec. 7, 1999).

Jackston et al., Journal of Cellular Biochemistry Supplement 38:1-6 (May 16, 2002).

Orlic et al., Annalsof the New York Academy of Sciences 938: 221-230 (Jun. 2001).

Orlic, International Journal of Hematology, 76 Suppl. 1: 144-145 (Aug. 2002).

SELECTED CELL DELIVERY FOR HEART FAILURE

RELATED APPLICATION

This application is a continuation of U.S. Ser. No. 10/198,101 filed on Jul. 19, 2001, now U.S. Pat. No. 7,097,833, which is hereby incorporated by reference in its entirety by reference thereto.

This invention is directed to methods of increasing blood flow to tissue in a subject by direct transplantation into or adjacent to such tissue of autologous lineage negative (Lin⁻) mononuclear cells or of side population (SP) cells, stem cells which may be isolated from adult organs, as well from hematopoietic sources such as blood and bone marrow, as a subset of Lin⁻ mononuclear cells; methods of regenerating tissue in a subject; methods of treating diseased tissue in a subject; methods of increasing angiogenesis and myogenesis in diseased or damaged tissue; methods of forming new blood vessels in tissue and new tissue, such as myocardial tissue, in diseased or damaged tissue such as ischemic heart tissue or coronary blood vessels in a subject; and methods of preventing heart failure in a subject and uses of such methods to treat disease or injury wherein ischemic tissue is present and where angiogenesis and myogenesis is desired. The methods described are also applicable for formation of blood vessels and new tissue in non-cardiovascular tissues.

BACKGROUND OF THE INVENTION

Delivery of cells to the myocardium has shown promise for the treatment of heart failure patients. The specific cell type or types which will be most effective as treatment are currently under study.

Recently, implantation of the bone marrow mononuclear cell fraction to the ischemic heart has resulted in positive histological and functional cardiac improvement. (Kamihata H. et al. *Circulation* 2001; 104(9):1046-1052) However, the mononuclear cell fraction contains cell types other than stem and progenitor cells, e.g., monocytes and lymphocytes, potentially resulting in lower effectiveness and increased inflammatory response. More specific selection methods, e.g., isolation of stem cells which only express the stem cell marker CD34+, leave out some of the most primitive stem cells. (Dao MA and Nolta JA *Leukemia* 2000; 14:773-776) Other recent studies have determined that local injection of lineage negative c-kit⁺ bone marrow cells from transgenic mice expressing enhanced green fluorescent protein into the contracting wall bordering infarcted myocardium resulted in myocardial regeneration, wherein the developing tissue comprised proliferating myocytes and vascular structures. (Orlic D. et al. *Nature* 2001; 401(6829):701-705)

Other recent studies have determined that local injection of lineage negative c-kit$^{POS}$ bone marrow cells from transgenic mice expressing enhanced green fluorescent protein into the contracting wall bordering infarcted myocardium resulted in myocardial regeneration, wherein the developing tissue comprised proliferating myocytes and vascular structures. (Orlic D. et al. Nature 2001; 401(6829):701-705)

Additional investigations have found that transplantation of highly enriched adult hematopoietic stem cells, called side population (SP) cells into lethally irradiated mice subsequently rendered ischemic by coronary artery occlusion followed by reperfusion resulted in migration of SP cells (CD34−/low, c-kit+, Sca+) or their progeny into ischemic cardiac muscle and blood vessels, differentiation to cardiomyocytes and endothelial cells, and contribution to the formation of functional tissue. (Jackson K. A. et al. *J. Clin. Investig.* 2001 107(11):1395-1402) The SP cells were selected by lack of nuclear staining with Hoechst dye and were additionally tested for c-Kit expression and PECAM-1 (CD31) expression. (Jackson K. A. et al. *J. Clin. Investig.* 2001)

Therefore, delivery of all lineage negative (Lin⁻) mononuclear cells, i.e., cells which do not exhibit phenotypic characteristics of any committed or terminally differentiated cell type, or the side population (SP) cells subset of the Lin⁻ mononuclear cells, will conserve all relevant stem cells and obviate the current use of additional specific selection methods.

Accordingly, the present invention discloses that transplantation of autologous lineage negative (Lin⁻) mononuclear cells or side population (SP) cells, which is a subset of cells within the Lin⁻ mononuclear cell population or which may be isolated from other organs such as skeletal muscle, cardiac muscle, liver and kidney, directly into or adjacent to diseased or injured tissue, e.g., the myocardium, results in engraftment of the transplanted Lin⁻ mononuclear cells or side population cells, their differentiation into cardiomyocytes and/or endothelial cells, and formation of functional tissue. The use of Lin⁻ mononuclear cells, or alternatively, SP cells, maintains a therapeutically valuable population of stem and progenitors by excluding differentiated and committed cell types without unnecessary additional processing for identification of specific stem cell markers.

Isolation of autologous lineage negative mononuclear cells or side population cells from the bone marrow (Lin⁻ BM-MNCs) or peripheral blood containing uncommitted or undifferentiated mononuclear cells (Lin⁻ MNCs) or isolation of side population (SP) cells from nonhematopoietic tissues and the direct delivery of such Lin⁻ mononuclear cells or side population cells to tissues such as the myocardium or coronary blood vessels, as provided by the present invention, is a novel therapeutic strategy for heart failure in adult mammals. Such a strategy is also useful for treatment of other types of tissue in need of neovascularization, e.g., skeletal muscle.

SUMMARY OF THE INVENTION

This invention provides methods of increasing blood flow to tissue in a subject in need thereof, methods of regenerating tissue in a subject, methods of treating diseased tissue in a subject, methods of forming new blood vessels in tissue and new tissue in a subject in need thereof, methods of increasing angiogenesis in diseased tissue in a subject, methods of forming new myocardial tissue in a subject in need thereof, and methods of preventing heart failure in a subject which comprise: a) isolating autologous mononuclear cells from the subject; b) selecting from the isolated autologous mononuclear cells of step (a) lineage negative (Lin⁻) mononuclear cells; and c) transplanting locally into or adjacent to the tissue an effective amount of the Lin⁻ autologous mononuclear cells, resulting in formation of new blood vessels in the tissue and formation of new tissue.

This invention also provides methods of increasing blood flow to tissue in a subject in need thereof, methods of regenerating tissue in a subject, methods of treating diseased tissue in a subject, methods of forming new blood vessels in tissue and new tissue in a subject in need thereof, methods of increasing angiogenesis in diseased tissue in a subject, methods of forming new myocardial tissue in a subject in need thereof, and methods of preventing heart failure in a subject which comprise: a) obtaining a cell suspension from the tissue or a second tissue of the subject; b) selecting from the cell suspension step (a) side population (SP) cells; and c) transplanting locally into or adjacent to the tissue an effective amount of the SP cells, resulting in formation of new blood vessels in the tissue and formation of new tissue.

This invention further provides methods of increasing blood flow to tissue in a subject in need thereof, methods of regenerating tissue in a subject, methods of treating diseased tissue in a subject, methods of forming new blood vessels in tissue and new tissue in a subject in need thereof, methods of increasing angiogenesis in diseased tissue in a subject, methods of forming new myocardial tissue in a subject in need thereof and methods of preventing heart failure in a subject which comprise: a) isolating autologous mononuclear cells from the subject; b) selecting from the isolated autologous mononuclear cells of step (a) lineage negative (Lin$^-$) mononuclear cells; c) selecting from the Lin$^-$ mononuclear cells of step (b) side population (SP) cells; and d) transplanting locally into or adjacent to the tissue an effective amount of the Lin$^-$ SP cells, resulting in formation of new blood vessels in the tissue and formation of new tissue.

DETAILED DESCRIPTION OF THE INVENTION

The present invention provides a method of increasing blood flow to tissue in a subject in need thereof, which comprises: a) isolating autologous mononuclear cells from the subject; b) selecting from the isolated autologous mononuclear cells of step (a) lineage negative (Lin.sup.−) mononuclear cells; and c) transplanting locally into or adjacent to the tissue an effective amount of the Lin.sup.− autologous mononuclear cells, resulting in formation of new blood vessels in the tissue and formation of new tissue, thereby increasing blood flow to the tissue.

The present invention also provides a method of regenerating tissue in a subject in need thereof, which comprises: a) isolating autologous mononuclear cells from the subject; b) selecting from the isolated autologous mononuclear cells of step (a) lineage negative (Lin$^-$) mononuclear cells; and c) transplanting locally into or adjacent to the tissue an effective amount of the Lin$^-$ autologous mononuclear cells, resulting in formation of new blood vessels in the tissue and the formation of new tissue in the subject, thereby regenerating the tissue in the subject.

The present invention further provides a method of treating diseased tissue in a subject in need thereof, which comprises: a) isolating autologous mononuclear cells from the subject; b) selecting from the isolated autologous mononuclear cells of step (a) lineage negative (Lin$^-$) mononuclear cells; and c) transplanting locally into or adjacent to the tissue an effective amount of the Lin$^-$ autologous mononuclear cells, resulting in formation of new blood vessels in the tissue and formation of new tissue, thereby treating the diseased tissue in the subject.

The present invention also provides a method of forming new blood vessels in tissue in a subject in need thereof, which comprises: a) isolating autologous mononuclear cells from the subject; b) selecting from the isolated autologous mononuclear cells of step (a) lineage negative (Lin$^-$) mononuclear cells; and c) transplanting locally into or adjacent to the tissue an effective amount of the Lin$^-$ autologous mononuclear cells, resulting in formation of new blood vessels in the tissue.

The present invention provides a method of forming new tissue in a subject in need thereof, which comprises: a) isolating autologous mononuclear cells from the subject; b) selecting from the isolated autologous mononuclear cells of step (a) lineage negative (Lin$^-$) mononuclear cells; and c) transplanting locally into or adjacent to the tissue an effective amount of the Lin$^-$ autologous mononuclear cells, resulting in formation of new tissue in the subject.

In a preferred embodiment of any of the methods provided by the present invention, the autologous mononuclear cells may be isolated in step (a) from either the bone marrow of the subject or from the peripheral blood of the subject.

In a preferred embodiment, the mononuclear cells may be isolated from the peripheral blood of the subject (or HLA-typed identical donor) using apheresis using known methods. In order to increase the concentration of progenitor and stem cells in the peripheral blood the subject is treated about 5 days before the apheresis procedure with a cytokine, including but not limited to G-CSF, GM-CSF or SCF (stem cell factor), thereby increasing the concentration of Lin$^-$ mononuclear cells and SP cells isolated therefrom.

In preferred embodiments of the methods described herein, the methods may further comprise: i) selecting from the Lin$^-$ mononuclear cells of step (b) side population cells; and ii) transplanting locally into or adjacent to the tissue an effective amount of the Lin$^-$ side population cells. In another preferred embodiment of the methods provided, the tissue is ischemic tissue. The ischemic tissue may be cardiac muscle tissue, for treatment of heart failure and cardiac improvement or skeletal muscle tissue. In additional preferred embodiments of the methods set forth herein, the tissue is damaged tissue. The damaged tissue may be heart muscle, skeletal muscle, brain, kidney, liver, an organ of the gastrointestinal tract, a coronary blood vessel, a peripheral blood vessel, an atrophied muscle, skin or lung. In other embodiments the damaged tissue may be an artificially created site, e.g., in injuries created by surgery, transplants or accidents. In another preferred embodiment of the presently provided methods, the coronary blood vessel is a compromised or occluded coronary blood vessel and the peripheral blood vessel is a compromised or occluded peripheral blood vessel. As used herein, a compromised blood vessel is a blood vessel that is injured, e.g., by disease, trauma or surgery, and whose ability to deliver blood to a particular tissue is less than optimal when compared to a healthy blood vessel of the same type. Preferably, the subject is a mammal. Most preferably, the mammal is a human. In further embodiment of the described methods, the new blood vessels comprise capillaries or collateral vessels.

In the methods of the subject invention, autologous bone-marrow is isolated from the subject usually under general anesthesia by aspiration from the tibia, femur, ilium or sternum with a syringe, preferably containing 1 mL heparin with an 18-gauge needle. Bone-marrow mononuclear cells are isolated using standard techniques with which one of skill is familiar; such techniques may be modified depending upon the species of the subject from which the cells are isolated. The marrow cells are transferred to a sterile tube and mixed with an appropriate amount of medium, e.g., 10 mL culture medium (Iscove's modified Dulbecco medium IMDM with 10% fetal bovine serum, penicillin G [100 U/mL] and streptomycin [100 Φg/mL]). The tube is centrifuged to pellet the bone marrow cells, e.g., at 2000 rpm for five minutes and the cell pellet re-suspended in medium, e.g., 5 mL culture medium. Low density bone-marrow mononuclear cells are separated from the suspension, e.g., by density gradient centrifugation over Histopaque-1083.™ (Sigma), e.g., as described by Yablonka-Reuveni and Nameroff and hereby incorporated by reference. (*Histochemistry* (1987) 87:27-38). Briefly, the cell suspension is loaded on 20% to 60% gradient, e.g., Histopaque-1083™ (Sigma), Ficoll-Hypaque or Percoll (both available from Pharmacia, Uppsala, Sweden) according to manufacturer's instructions and as described by Yablonka-Reuveni and Nameroff. For example, the cells are centrifuged at 400 g for 20 minutes for Ficoll-Hypaque or at 2000 rpm for 10 minutes for Percoll. Following centrifugation, the top two-thirds of total volume are transferred into a tube, as these layers contain most of the low density bone-marrow mono-nuclear cells. The cells are centrifuged, e.g., at 2000 rpm for 10 minutes to remove the Histopaque. This is repeated and the cell pellet of bone-marrow mononuclear cells is re-suspended in culture medium or buffer, e.g., IMDM, saline, phosphate buffered saline, for transplantation. Preferably, fresh bone-marrow mononuclear cells, isolated as described above, are used for isolation of the Lin⁻ bone-marrow mononuclear cells to be used for transplantation.

Lin⁻ bone marrow mononuclear cells are preferably selected using two processes. First, mononuclear cells are separated from the bone marrow sample by centrifugation with a density gradient (e.g., Ficoll-Paque, Ficoll-Hypaque) and removing the layer of white cells above the density gradient layer, as described above. Second, terminally differentiated hematopoietic cells are removed from the mononuclear fraction by incubating this fraction with detectable molecules e.g., by fluorescence or conjugation to a magnetic particle, including but not limited to antibodies, which molecules bind to cell-surface markers specific for lineage committed cells; detecting the lineage committed cells bound to such molecules by the binding of the molecules to a substrate; and removing these molecule-bound cells by cell sorting techniques e.g., flow assisted cell sorting (FACS) or a magnetic selection protocol. The remaining cells are the desired Lin– bone marrow mononuclear cells. Side population cells are contained within this cell population and are isolated from Lin– bone marrow mononuclear cells as described in Example 2, infra.

Alternatively, side population cells may be isolated from tissues sources other than the mononuclear cell fraction of the bone marrow or of the peripheral blood, e.g., from skeletal muscle, cardiac muscle, liver or kidney, as also described in Example 2. The tissue source of SP cells may be the same tissue into which the isolated side population will be transplanted or from a unrelated tissue, e.g., SP cells from skeletal tissue for transplantation into cardiac muscle.

Cell surface markers which may be used for detecting and excluding lineage committed cells include but are not limited to MAC-1 for monocytes/macrophages; CD4, CD5, CD8 for T-lymphocytes, CD5, B220 for B-lymphocytes, GR-1 for granulocytes and TER-119 for erythroid cells using readily available commercial antibodies specific for the respective markers. In addition, markers of specific types of differentiated cells may also be used for further exclusion of differentiated and lineage committed cells for which antibodies are also available, e.g., desmin and α-actinin for cardiac muscle; ICAM-2, VE-cadherin, vWF, and factor VIII for differentiated vascular endothelial cells, and Flk-1 and Flt-1, receptors of VEGF for early endothelial progenitor cells. The concentrations of the different lineage specific molecules used are sufficient to mark a majority of the lineage committed cells.

The autologous Lin⁻ mononuclear cells isolated from bone-marrow or peripheral blood, or the side (SP) population cells isolated from such Lin⁻ mononuclear cells or isolated from tissue other than mononuclear cells, are transplanted by injection or by alternative means of delivery, as described infra, e.g., into the center, bordering zone, or neighboring areas of the ischemic tissue, e.g., the myocardium, coronary blood vessels or peripheral blood vessels. Transplantation of the autologous Lin⁻ mononuclear cells or the side (SP) population cells may be to the adjacent or near tissue, which is defined herein as an area of tissue near or within 5 to 10 mm of the transplantation target site, so as to enable the transplanted cells to migrate to such site. Transplantation to the adjacent tissue will depend on the density of the target tissue.

In additional embodiments of the present invention, the autologous Lin⁻ mononuclear cells or the side (SP) population cells may be transplanted into or adjacent to any site of any tissue in which angiogenesis or repair is desired. Such tissue includes but is not limited to underperfused tissue of any end-organ, e.g., tissues with chronic ischemia. Such underperfused tissue includes but is not limited to the heart, brain, skeletal muscle, kidney, liver, organs of the gastrointestinal tract and other organs and tissues requiring repair.

The transplanted autologous Lin⁻ mononuclear cells or the side (SP) population cells are delivered to the desired tissue site(s) in an effective amount of approximately $1 \times 10^5$ cells to about $1 \times 10^{10}$ cells, preferably about $1 \times 10^7$ cells to about $1 \times 10^8$ cells, per injection site, preferably by needle injection. Preferably, a tissue in need thereof receives a total of about fifty injections, e.g., for a leg or arm, and about ten injections into heart muscle. Alternatively, the autologous Lin⁻ mononuclear cells or the side (SP) population cells are delivered by intravascular injection or infusion into arteries or veins, endoluminal injection directly into an occlusion, retrograde perfusion, pericardial delivery, implants (biodegradable or biostable), e.g., local implant scaffold, patch, needle-free injection using propulsion by gas such as $CO_2$ usually for softer tissue such as mucosal, neural or adipose tissue, acceleration or transfer into tissue by other means such as iontophoresis or electroporation, pressure or application to a tissue or organ surface. In general, delivery may be accomplished with the use of any medical device for delivery of transplanted cells.

In preferred embodiments of any of the methods described herein, the tissue or adjacent tissue into which autologous Lin⁻ mononuclear cells or the side (SP) population cells are transplanted includes any diseased or damaged tissue and any tissue in need of repair or regeneration, including but not limited to underperfused tissue such as tissue found in chronic ischemia. Preferably, the tissue includes but is not limited to ischemic tissue. More preferably the tissue includes such tissue as cardiac muscle tissue, skeletal muscle tissue, brain tissue e.g., affected by stroke or AV malformations, coronary vessels, kidney, liver, organs of the gastrointestinal tract, muscle tissue afflicted by atrophy, including neurologically based muscle atrophy. In further embodiments the subject is preferably a mammal. Most preferably, the mammal is a human.

In the present invention, autologous Lin⁻ mononuclear cells (MNCs) or the side (SP) population cells are locally transplanted into or adjacent to ischemic tissues. There are several advantages of local transplantation rather than intravenous transfusion of MNCs or SPs for therapeutic neovascularization. First, through local transplantation, one can increase the density of Lin⁻ MNCs or the side (SP) population cells at the target tissue compared with intravenous infusion. This may be an advantage for cell survival in the tissues, because it is believed that cells must form clusters to survive in tissues. Second, local transplantation may reduce the systemic side effects of transplanted Lin⁻ MNCs or the side (SP) population cells compared with systemic infusion. Systemic intravenous administration of Lin⁻ MNCs or the side (SP) population cells may potentially elicit adverse effects on angiogenic disorders such as cancers, rheumatoid arthritis, and diabetic retinopathy.

In the present invention autologous Lin⁻ MNCs or the side (SP) population cells are transplanted into or adjacent to an ischemic tissue where they become incorporated into or participate in the formation of new blood vessels and/or capillaries. Lin⁻ MNCs or the side (SP) population cells may be detectably labeled, e.g., by fluorescence, for examination of incorporation into the desired tissue.

The present invention additionally provides a method of increasing angiogenesis in diseased tissue in a subject, which comprises: a) isolating autologous mononuclear cells from the subject; b) selecting from the isolated autologous mononuclear cells of step (a) lineage negative (Lin⁻) mononuclear cells; and c) transplanting locally into or adjacent to the tissue an effective amount of the Lin⁻ autologous mononuclear cells, resulting in formation of new blood vessels in the tissue and the formation of new tissue, thereby increasing angiogenesis in the diseased tissue.

The present invention provides a method of preventing heart (myocardial) failure in a subject in need thereof, which comprises: a) isolating autologous mononuclear cells from the subject; b) selecting from the isolated autologous mononuclear cells of step (a) lineage negative (Lin⁻) mononuclear cells; and c) transplanting locally into or adjacent to the tissue an effective amount of the Lin⁻ autologous mononuclear cells, resulting in formation of new blood vessels in the myocardial tissue and the formation of new myocardial tissue, thereby preventing heart failure in the subject.

The present invention additionally provides a method of forming new blood vessels in tissue in a subject in need thereof, which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into or adjacent to the tissue an effective amount of the Lin⁻ SP cells, resulting in formation of new blood vessels in the tissue.

The present invention also provides a method of forming new myocardial tissue in a subject in need thereof, which comprises: a) isolating autologous mononuclear cells from the subject; b) selecting from the isolated autologous mononuclear cells of step (a) lineage negative (Lin⁻) mononuclear cells; and c) transplanting locally into myocardial tissue an effective amount of the Lin⁻ autologous mononuclear cells, resulting in formation of new myocardial tissue.

The present invention additionally provides another method of forming new tissue in a subject in need thereof, which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into the tissue an effective amount of the Lin⁻ SP cells, resulting in formation of new tissue.

The present invention additionally provides another method of forming new myocardial tissue in a subject in need thereof, which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into myocardial tissue an effective amount of the Lin⁻ SP cells, resulting in formation of new myocardial tissue.

This invention further provides a method of increasing blood flow to tissue in a subject in need thereof, which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into or adjacent to the tissue an effective amount of the Lin⁻ SP cells, resulting in formation of new blood vessels in the tissue and formation of new tissue, thereby increasing blood flow to the tissue.

The present invention further provides a method of treating diseased tissue in a subject in need thereof, which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into or adjacent to the tissue an effective amount of the Lin⁻ SP cells, resulting in formation of new blood vessels in the tissue and formation of new tissue, thereby treating the diseased tissue in the subject.

This invention also provides a method of increasing angiogenesis in diseased tissue in a subject, which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into or adjacent to the tissue an effective amount of the Lin⁻ SP cells, resulting in formation of new blood vessels in the tissue and formation of new tissue, thereby increasing angiogenesis in the diseased tissue.

This invention further provides a method of preventing heart (myocardial) failure in a subject in need thereof, which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into or adjacent to the tissue an effective amount of the Lin⁻ SP cells, resulting in formation of new blood vessels in the tissue and formation of new myocardial tissue, thereby preventing heart failure in a subject.

This invention additionally provides a method of regenerating tissue in a subject which comprises: a) isolating autologous mononuclear cells from the subject; b) selecting from the isolated autologous mononuclear cells of step (a) lineage negative (Lin⁻) mononuclear cells; c) selecting from the Lin⁻ mononuclear cells of step (b) side population (SP) cells; and d) transplanting locally into or adjacent to the tissue an effective amount of the Lin⁻ SP cells, resulting in formation of new blood vessels in the tissue and the formation of new tissue, thereby regenerating the tissue in the subject.

This invention further provides a method of increasing blood flow to tissue in a subject in need thereof, which comprises: (a) obtaining a cell suspension from the tissue or a second tissue of the subject; (b) selecting from the cell suspension of step (a) side population (SP) cells; and (c) transplanting locally into or adjacent to the tissue an effective amount of the SP cells, resulting in formation of new blood vessels in the tissue and formation of new tissue, thereby increasing blood flow to the tissue.

This invention additionally provides a method of regenerating tissue in a subject which comprises: (a) obtaining a cell suspension from the tissue or a second tissue of the subject; (b) selecting from the cell suspension of step (a) side population (SP) cells; and (c) transplanting locally into or adjacent to the tissue an effective amount of the SP cells, resulting in formation of new blood vessels in the tissue and formation of new tissue, thereby regenerating the tissue.

The present invention further provides a method of treating diseased tissue in a subject in need thereof, which comprises: (a) obtaining a cell suspension from the tissue or a second tissue of the subject; (b) selecting from the cell suspension of step (a) side population (SP) cells; and (c) transplanting locally into or adjacent to the tissue an effective amount of the SP cells, resulting in formation of new blood vessels in the tissue and formation of new tissue, thereby treating the diseased tissue.

The present invention additionally provides a method of forming new blood vessels in tissue in a subject in need thereof, which comprises: (a) obtaining a cell suspension from the tissue or a second tissue of the subject; (b) selecting from the cell suspension of step (a) side population (SP) cells; and (c) transplanting locally into or adjacent to the tissue an effective amount of the SP cells, resulting in formation of new blood vessels in the tissue.

The present invention also provides a method of forming new tissue in a subject in need thereof, which comprises: (a) obtaining a cell suspension from the tissue or a second tissue of the subject; (b) selecting from the cell suspension of step (a) side population (SP) cells; and (c) transplanting locally into or adjacent to the tissue an effective amount of the SP cells, resulting in formation of new tissue.

The present invention also provides a method of forming new myocardial tissue in a subject in need thereof, which comprises: (a) obtaining a cell suspension from the myocardial tissue or a second tissue of the subject; (b) selecting from the cell suspension of step (a) side population (SP) cells; and (c) transplanting locally into or adjacent to the myocardial tissue an effective amount of the SP cells, resulting in formation of new blood vessels in the tissue and formation of new tissue, thereby forming new myocardial tissue.

This invention also provides a method of increasing angiogenesis in diseased tissue in a subject, which comprises: (a) obtaining a cell suspension from the tissue or a second tissue of the subject; (b) selecting from the cell suspension of step (a) side population (SP) cells; and (c) transplanting locally into or adjacent to the tissue an effective amount of the SP cells, resulting in formation of new blood vessels in the tissue and formation of new tissue, thereby increasing angiogenesis in the diseased tissue.

This invention further provides a method of preventing heart (myocardial) failure in a subject in need thereof, which comprises: (a) obtaining a cell suspension from the myocardial tissue or a second tissue of the subject; (b) selecting from the cell suspension of step (a) side population (SP) cells; and (c) transplanting locally into or adjacent to the tissue an effective amount of the SP cells, resulting in formation of new blood vessels in the tissue and formation of new tissue, thereby preventing heart (myocardial) failure.

The invention will be better understood from the examples which follow, however the invention is not limited to these examples, which are solely intended to be illustrative thereof.

EXAMPLE 1

Autologous Lin⁻ Bone Marrow Mononuclear Cell Selection and Transplantation for Treatment of Heart Failure and Improvement of Cardiac Function Bone marrow is aspirated from the subject, i.e., a patient or donor. A donor may be used only if the subject and donor have been HLA-type matched to be identical. In the methods of the subject invention, autologous bone-marrow is isolated from the subject usually under general anesthesia by aspiration from the tibia, femur, ilium or sternum with a syringe, preferably containing 1 mL heparin with an 18-gauge needle. Bone-marrow mononuclear cells are isolated using standard techniques with which one of skill is familiar; such techniques may be modified depending upon the species of the subject from which the cells are isolated. The marrow cells are transferred to a sterile tube and mixed with an appropriate amount of medium, e.g., 10 mL culture medium (Iscove's modified Dulbecco medium IMDM with 10% fetal bovine serum, penicillin G [100 U/mL] and streptomycin [100 Φg/mL]). The tube is centrifuged to pellet the bone marrow cells, e.g., at 2000 rpm for five minutes and the cell pellet resuspended in medium, e.g., 5 mL culture medium. Low density bone-marrow mononuclear cells are separated from the suspension, e.g., by density gradient centrifugation over Histopaque-1083™ (Sigma), e.g. as described by Yablonka-Reuveni and Nameroff and hereby incorporated by reference. (Histochemistry (1987) 87:27-38). Briefly, the cell suspension is loaded on 20% to 60% gradient, e.g. Histopaque-1083™ (Sigma), Ficoll-Hypaque or Percoll (both available from Pharmacia, Uppsala, Sweden) according to manufacturer's instructions and as described by Yablonka-Reuveni and Nameroff. For example, the cells are centrifuged at 400 g for 20 minutes for Ficoll-Hypaque or at 2000 rpm for 10 minutes for Percoll. Following centrifugation, the top two-thirds of total volume are transferred into a tube, as these layers contain most of the low density bone-marrow mononuclear cells. The cells are centrifuged, e.g. at 2000 rpm for 10 minutes to remove the Histopaque. This is repeated and the cell pellet of bone-marrow mononuclear cells is resuspended in culture medium or buffer, e.g., IMDM, saline, phosphate buffered saline, for transplantation. Preferably, fresh bone-marrow mononuclear cells, isolated as described above, are used for isolation of the Lin⁻ bone-marrow mononuclear cells to be used for transplantation.

Lin⁻ bone marrow mononuclear cells are preferably selected using two processes. First, mononuclear cells are separated from the bone marrow sample by centrifugation with a density gradient (e.g., Ficoll-Paque, Ficoll-Hypaque) and removing the layer of white cells above the density gradient layer, as described above. Second, terminally differentiated hematopoietic cells are removed from the mononuclear fraction by incubating this fraction with detectable molecules e.g., by fluorescence or conjugation to a magnetic particle, including but not limited to antibodies, which molecules bind to cell-surface markers specific for lineage committed cells; detecting the lineage committed cells bound to such molecules by the binding of the molecules to a substrate; and removing these molecule-bound cells by cell sorting techniques e.g., flow assisted cell sorting (FACS) or a magnetic selection protocol. The remaining cells are the desired Lin– bone marrow mononuclear cells. Side population cells are contained within this cell population. (See Example 2)

In another preferred embodiment, the mononuclear cells may be isolated from the peripheral blood of the subject (or HLA-typed identical donor) using apheresis e.g., as described by Haas R., et al. *Exp. Hematol.* 1990 February; 18(2):94-98. Typically, the concentration of progenitor and stem cells in the peripheral blood is increased by treating the subject with a cytokine, including but not limited to G-CSF, GM-CSF or SCF (stem cell factor), about 5 days prior to the apheresis procedure, thereby increasing the concentration of Lin⁻ mononuclear cells and SP cells isolated therefrom.

Cell surface markers for lineage committed cells include but are not limited to MAC-1 for monocytes/macrophages; CD4, CD5, CD8 for T-lymphocytes, CD5, B220 for B-lymphocytes, GR-1 for granulocytes and TER-119 for erythroid cells. Markers of specific types of differentiated cells, e.g., desmin and α-actinin for cardiac muscle; ICAM-2, VE-cadherin, vWF, and factor VIII for differentiated vascular endothelial cells, and Flk-1 and Flt-1, receptors of VEGF for early endothelial progenitor cells may also be used. The concentrations of the different lineage specific molecules, e.g., antibodies, are sufficient to mark a majority of the lineage committed cells.

Antibodies which may be used to select for lineage committed cells which are then removed include but are not limited to biotin conjugated anti-CD4, anti-CD5, anti-CD6, anti-CD45 (anti-B220) and anti-CD54 (anti-MAC-1) (Research Diagnostics Inc., Flanders, N.J.); M1/70 (anti-MAC-1; rat IgG2) (Pharmingen, San Diego, Calif.) ; hybridoma RB6-8C5 (anti-Gr-1; rat IgG2b from R. L. Coffinan, DNAX, Palo Alto, Calif.); TER-119 (anti-erythrocytes; rat IgG2b; from T. Kina, Kyoto University); hybridoma 14.8 (anti-B220; rat IgG2b from American Type Culture Collection (Rockville, Md.)

The autologous Lin$^-$ mononuclear cells isolated from the bone-marrow or the peripheral blood are transplanted by injection into the center, bordering zone, or neighboring areas of the ischemic tissue, e.g. the myocardium, coronary blood vessels or peripheral blood vessels.

In additional embodiments of the present invention, the autologous Lin$^-$ bone-marrow or peripheral-blood mononuclear cells may be transplanted into or adjacent to any site of any tissue in which angiogenesis or repair is desired, as described supra. Such tissue includes but is not limited to underperfused tissue of any end-organ, e.g., tissues with chronic ischemia. Such underperfused tissue includes but is not limited to the heart, brain, skeletal muscle, kidney, liver, organs of the gastrointestinal tract and other organs and tissues requiring repair.

EXAMPLE 2

Autologous Lin$^-$ Side Population (SP) Cell Selection and Transplantation for Transplantation for Treatment of Heart Failure and Improvement of Cardiac Function Side population (SP) cells may be isolated from tissues including but not limited to bone marrow, skeletal muscle, cardiac muscle, liver and kidney. If the bone marrow or peripheral blood are used as the source of SP cells, Lin$^-$ mononuclear cells are isolated from the source tissue, e.g., bone marrow or peripheral blood, as described in Example 1.

If tissue other than the bone marrow or peripheral blood is the source of SP cells, a tissue sample is obtained and digested according to known methods, e.g., as described by Nag A. C. and Zak R. *J. Anat.* 1979 October 129(3):541-559, so as to obtain a cell suspension. The tissue sample used as a source of SP cells may be from the same tissue into which the SP cells will be transplanted, e.g. cardiac muscle for transplantation into the heart, or may be from a second tissue, e.g., bone marrow or skeletal tissue may be used to obtain SP cells for use in transplantation into cardiac muscle. SP cells are isolated from the cell suspension after nuclear staining, e.g., Hoechst staining, as described below, using a cell sorter such as a flow cytometer, as described below. The isolated SP cells are delivered to the desired tissue site(s) in an effective amount, as set forth below for Lin$^-$ SP mononuclear cells by the same types of administration means as described herein for Lin$^-$ mononuclear cells and for Lin$^-$ SP mononuclear cells.

The SP subset within the isolated Lin$^-$ mononuclear cells are subsequently defined by staining with a nuclear dye, including but not limited to Hoechst dye 33342 or Rhodamine-123. The SP cells exclude nuclear staining and thus are selected by the absence of a strong fluorescent signal at one or more wavelengths. In mice, SP cells selected in this manner typically account for between 0.05% and 0.1% (Jackson 2001; Goodell 1996) of the cells isolated from whole bone marrow.

Briefly, the isolated Lin.sup.− mononuclear cells are resuspended at $10.\text{sup}.6$ cells per ml in prewarmed DMEM containing 2% FCS, in mM Hepes, penicillin, streptomycin, and 5 µg/ml Hoechst 33342 (Sigma-Aldrich, St. Louis, Mo.) and were incubated for 90 min at 37° C., as described previously for extracted bone marrow cells. (Goodell M. et al. *J. Exp. Med.* 1996; 183:1797-1806) After Hoechst staining, cells are pelleted and maintained at 4° C. before FACS analysis. (Beckton Dickinson & Co., Mountain View, Calif.) Whereas, current protocols include pre-enrichment for specific cell markers, e.g., Sca$^+$ using MACS® (Miltenyi Biotec, Sunnyvale, Calif.) and streptavidin microbeads, the methods of the present invention do not require additional processing.

Analysis and sorting is performed on a dual-laser FACStar Plus® flow cytometer (Beckton Dickinson & Co.), as described previously. (Goodell M. et al. J. Exp. Med. 1996) Alternatively, sorting and analysis of SP cells is performed on a triple-laser instrument (MoFlow; Cytomation Inc., Fort Collins, Colo.), as described previously. (Jackson K. A. et al. J. Clin. Investig. 2001) SP cell purity of greater than 91% is routinely achieved.

Briefly, the Hoechst dye is excited at 350 nm and its fluorescence is measured at two wavelengths using a 450 BP 20 (450/20 nm band pass filter) and a 675 EFLP (675 nm long pass edge filter) optical filter (Omega Optical Inc., Braffleboro, Vt.). A 610 DMSP (610 nm short pass dichroic mirror) is used to separate the emission wavelengths. Hoechst "blue" represents the 450 BP filter, the standard analysis wavelength for Hoechst 33342 DNA content analysis. The Lin$^-$ cells may be re-suspended in cold HBSS containing 2 µg/ml propidium iodide (PI) prior to cell sorting to facilitate exclusion of dead cells. In the methods of the present invention, Hoeschst dye may also be used without PI. Hoechst "red" represents the 675 EFLP filter. Cells positive for PI are seen to the far right of the Hoechst red and are excluded. The gating on forward and side scatter is not stringent; only erythrocytes and dead cells are excluded. Cells are sorted into glass tubes containing 100% FCS, and an aliquot is removed at the end of the sort to reanalyze and establish high purity. As described by Goodell (1996), the side population (SP) sorting gates are established as follows: a live gate is defined on the flow cytometer using Hoechst red and blue axes to exclude dead cells, red cells (no Hoechst stain), and debris. After counting $10^5$ events within this live gate, the SP population is able to be clearly defined. Sorted SP cells are washed in HBSS+ and counted for introduction into the recipients.

The isolated Lin$^-$ SP mononuclear cells are delivered to the desired tissue site(s) in an effective amount of approximately $1\times10^5$ cells to about $1\times10^{10}$ cells, preferably about $1\times10^7$ cells to about $1\times10^8$ cells, per injection site, preferably by needle injection, but not limited thereto, as described above for delivery of isolated autologous Lin.sup.− cells. Preferably, a tissue in need thereof receives a total of about fifty injections, e.g. for a leg or arm, and about ten injections into heart muscle. In general, delivery may be accomplished with the use of any medical device for delivery of transplanted cells.

Low Hoechst dye-staining or Rhodamine-123-staining cells contain the most primitive hematopoietic cells. (Goodell M., et al. *J. Exp. Med.* 1996; 183(4):1797-1806) Accordingly, no additional selection of stem cell subsets for specific stem cell markers is required, rendering the methods of the present invention advantageous over currently used laborious selection methods.

The selected Lin⁻ SP cells are delivered directly to the myocardium, coronary blood vessels or peripheral blood vessels by injection or other delivery routes, as described in Example 1, for treatment of heart failure. SP cells may also be injected into other tissue types in need thereof, e.g., skeletal muscle for treatment of disease or injury.

The foregoing description and examples detail specific methods which may be employed to practice the present invention. One of skill in the art will readily know and appreciate how to devise alternative reliable methods at arriving at the same information by using and/or modifying the disclosure of the present invention using ordinary skill. However, the foregoing description and examples should not be construed as limiting the overall scope of the present invention, but are to be considered as illustrative thereof. All documents and publications cited herein are expressly incorporated by reference into the subject application.

I claim:

1. A method of increasing blood flow to a tissue in a subject in need thereof which comprises:
    a) isolating autologous mononuclear cells from skeletal muscle from said subject;
    b) selecting from the isolated autologous mononuclear cells of step (a) lineage negative (Lin⁻) mononuclear cells; and
    c) transplanting locally into or adjacent to the tissue in said subject an effective amount of the Lin⁻ autologous mononuclear cells, resulting in formation of new blood vessels in the tissue and formation of new tissue, thereby increasing blood flow to the tissue in said subject.

2. The method of claim 1, further comprising:
    (i) selecting from the Lin⁻ mononuclear cells of step (b) side population (SP) cells; and
    (ii) transplanting locally into or adjacent to the tissue in said subject an effective amount of the Lin⁻ SP cells.

3. The method of claim 1, wherein the tissue is ischemic tissue in said subject.

4. The method of claim 3, wherein the ischemic tissue is cardiac muscle tissue or skeletal muscle tissue.

5. A method of increasing blood flow to a tissue in a subject in need thereof which comprises:
    a) obtaining a cell suspension from skeletal muscle of said subject;
    b) selecting from the cell suspension of step (a) side population (SP) cells; and
    c) transplanting locally into or adjacent to the tissue in said subject an effective amount of the SP cells, resulting in formation of new blood vessels in the tissue and formation of new tissue, thereby increasing blood flow to the tissue in said subject.

6. The method of claim 5, wherein the SP cells are selected by staining with a nuclear dye, wherein the SP cells exclude staining from nuclei.

7. The method of claim 6, wherein the tissue is ischemic tissue in said subject.

8. The method of claim 7, wherein the ischemic tissue is cardiac muscle tissue or skeletal muscle tissue.

9. A method of regenerating a tissue in a subject which comprises:
    a) isolating autologous mononuclear cells from skeletal muscle from said subject;
    b) selecting from the isolated autologous mononuclear cells of step (a) lineage negative (Lin⁻) mononuclear cells; and
    c) transplanting locally into or adjacent to the tissue in said subject an effective amount of the Lin⁻ autologous mononuclear cells, resulting in formation of new blood vessels in the tissue and formation of new tissue, thereby regenerating the tissue in said subject.

10. The method of claim 9, further comprising:
    (i) selecting from the Lin⁻ mononuclear cells of step (b) side population (SP) cells; and
    (ii) transplanting locally into or adjacent to the tissue in said subject an effective amount of the Lin⁻ SP cells.

11. The method of claim 9, wherein the tissue is ischemic tissue in said subject.

12. The method of claim 11, wherein the ischemic tissue is cardiac muscle tissue or skeletal muscle tissue.

13. A method of regenerating a tissue in a subject which comprises:
    a) obtaining a cell suspension from skeletal muscle of said subject;
    b) selecting from the cell suspension of step (a) side population (SP) cells; and
    c) transplanting locally into or adjacent to the tissue in said subject an effective amount of the SP cells, resulting in formation of new blood vessels in the tissue and formation of new tissue, thereby regenerating the tissue in said subject.

14. The method of claim 13, wherein the SP cells are selected by staining with a nuclear dye, wherein the SP cells exclude staining from nuclei.

15. The method of claim 13, wherein the tissue is ischemic tissue in said subject.

16. The method of claim 15, wherein the ischemic tissue is cardiac muscle tissue or skeletal muscle tissue.

17. A method of treating a diseased tissue in a subject which comprises:
    a) isolating autologous mononuclear cells from skeletal muscle from said subject;
    b) selecting from the isolated autologous mononuclear cells of step (a) lineage negative (Lin⁻) mononuclear cells; and
    c) transplanting locally into or adjacent to the tissue in said subject an effective amount of the Lin⁻ autologous mononuclear cells, resulting in formation of new blood vessels in the tissue and formation of new tissue, thereby treating the diseased tissue in said subject.

18. The method of claim 17, further comprising:
    (i) selecting from the Lin⁻ mononuclear cells of step (b) side population (SP) cells; and
    (ii) transplanting locally into or adjacent to the tissue in said subject an effective amount of the Lin⁻ SP cells.

19. The method of claim 17, wherein the tissue is ischemic tissue in said subject.

20. The method of claim 19, wherein the ischemic tissue is cardiac muscle tissue or skeletal muscle tissue.

21. A method of treating a diseased tissue in a subject which comprises:
    a) obtaining a cell suspension from skeletal muscle of said subject;
    b) selecting from the cell suspension of step (a) side population (SP) cells; and
    c) transplanting locally into or adjacent to the tissue in said subject an effective amount of the SP cells, resulting in formation of new blood vessels in the tissue and formation of new tissue, thereby treating the diseased tissue in said subject.

22. The method of claim 21, wherein the SP cells are selected by staining with a nuclear dye, wherein the SP cells exclude staining from nuclei.

23. The method of claim 21, wherein the tissue is ischemic tissue in said subject.

24. The method of claim 23, wherein the ischemic tissue is cardiac muscle tissue or skeletal muscle tissue.

* * * * *

UNITED STATES PATENT AND TRADEMARK OFFICE
CERTIFICATE OF CORRECTION

| | |
|---|---|
| PATENT NO. | : 7,658,915 B2 |
| APPLICATION NO. | : 11/493711 |
| DATED | : February 9, 2010 |
| INVENTOR(S) | : Freyman |

Page 1 of 1

It is certified that error appears in the above-identified patent and that said Letters Patent is hereby corrected as shown below:

Column 3, line 28, "Lin.sup.-" should be changed to --Lin$^-$--;

Column 3, line 30, "Lin.sup.-" should be changed to --Lin$^-$--;

Column 5, line 1, "400g" should be changed to --400 rpm--;

Column 5, line 28, "Lin-" should be changed to --Lin$^-$--;

Column 10, line 18, "400g" should be changed to --400 rpm--;

Column 12, line 4, "Lin.sup.-" should be changed to --Lin$^-$--;

Column 12, line 5, "10.sup.6" should be changed to --$10^6$--;

Column 12, line 28-29, "Braffleboro" should be changed to --Brattleboro--; and

Column 12, line 55, "Lin.sup.-" should be changed to --Lin$^-$--.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO.       : 7,658,915 B2                                    Page 1 of 1
APPLICATION NO.  : 11/493711
DATED            : February 9, 2010
INVENTOR(S)      : Toby Freyman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 743 days.

Signed and Sealed this

Thirtieth Day of November, 2010

David J. Kappos
*Director of the United States Patent and Trademark Office*